United States Patent
DiMatteo et al.

(10) Patent No.: US 7,320,703 B2
(45) Date of Patent: Jan. 22, 2008

(54) METHOD FOR INSERTING A PROSTHESIS

(76) Inventors: Kristian DiMatteo, 25 Carleton Rd., Waltham, MA (US) 02541; Robert Thistle, 655 East St., Brockton, MA (US) 02302; John Spiridigliozzi, 125 Dana Ave., Hyde Park, MA (US) 02136

( * ) Notice: Subject to any disclaimer, the term of this patent is extended or adjusted under 35 U.S.C. 154(b) by 210 days.

(21) Appl. No.: 11/077,890

(22) Filed: Mar. 11, 2005

(65) Prior Publication Data
US 2005/0228476 A1  Oct. 13, 2005

Related U.S. Application Data

(62) Division of application No. 10/176,834, filed on Jun. 21, 2002, now abandoned.

(51) Int. Cl.
*A61F 2/06* (2006.01)
(52) U.S. Cl. ...................... 623/1.12; 623/903
(58) Field of Classification Search ....... 623/1.23–1.35
See application file for complete search history.

(56) References Cited

U.S. PATENT DOCUMENTS

| | | |
|---|---|---|
| 4,140,126 A | 2/1979 | Choudhury |
| 4,577,631 A | 3/1986 | Kreamer |
| 4,617,932 A | 10/1986 | Kornberg |
| 4,950,227 A | 8/1990 | Savin et al. |
| 5,405,378 A | 4/1995 | Strecker |
| 5,464,449 A | 11/1995 | Ryan et al. |
| 5,591,229 A | 1/1997 | Parodi |
| 5,647,857 A | 7/1997 | Anderson et al. |
| 5,755,770 A | 5/1998 | Ravenscroft |

(Continued)

FOREIGN PATENT DOCUMENTS

JP  7163299  6/2001

(Continued)

OTHER PUBLICATIONS

Lawrence, DD Jr., Charnsangavej C, Wright KC, Gianturco C, Wallace S. *Percutaneous Endovascular Graft: Experimental Evaluational*: Radiology May 1987; 163 (2): 357-60.

(Continued)

*Primary Examiner*—Suzette Gherbi
(74) *Attorney, Agent, or Firm*—RatnerPrestia

(57) ABSTRACT

A graft system for intraluminal delivery in a vessel in need of repair comprising a graft, anchoring means, and a strippable sheath around at least part of the graft. A preferred anchoring means is a balloon-expandable stent. Also included in the invention is a method of using the device to treat a body lumen. The strippable sheath is removable by pulling on a drawstring to remove it which permits expansion of the graft. The positioning of the device may then be adjusted prior to stent dilation. A preferred embodiment of the invention includes a bifurcated graft system for intraluminal delivery in an aortic aneurysm comprising a bifurcated graft having a distal region and two legs, an expandable stent disposed in part of the distal region, and a strippable crocheted sheath around the distal region and one of the two legs. The strippable crocheted sheath is removable by untying it to permit expansion of the graft after initial placement within the aneurysm.

4 Claims, 15 Drawing Sheets

U.S. PATENT DOCUMENTS

| | | | |
|---|---|---|---|
| 5,824,055 | A | 10/1998 | Spridigliozzi et al. |
| 5,919,225 | A | 7/1999 | Lau et al. |
| 5,954,764 | A | 9/1999 | Parodi |
| 6,019,785 | A | 2/2000 | Strecker |
| 6,036,723 | A | 3/2000 | Anidjar et al. |
| 6,096,027 | A | 8/2000 | Layne |
| 6,102,918 | A | 8/2000 | Kerr |
| 6,235,051 | B1 | 5/2001 | Murphy |
| 6,261,316 | B1 | 7/2001 | Shaolian et al. |
| 6,302,891 | B1 | 10/2001 | Nadal |
| 6,315,792 | B1 | 11/2001 | Armstrong et al. |
| 6,344,054 | B1 | 2/2002 | Parodi |
| 6,352,553 | B1 * | 3/2002 | van der Burg et al. .... 623/1.23 |
| 6,352,561 | B1 * | 3/2002 | Leopold et al. ............ 623/1.23 |
| RE38,091 | E | 4/2003 | Strecker |
| 2002/0007208 | A1 | 1/2002 | Strecker |

FOREIGN PATENT DOCUMENTS

| | | |
|---|---|---|
| JP | 2001211811 | 8/2001 |
| JP | 2001211812 | 8/2001 |
| WO | WO 01/10351 A1 | 2/2001 |

OTHER PUBLICATIONS

Parodi JC, Palmaz JC, Barone HD. *Transfemoral intraluminal graft implantation for abdominal aortic aneurysms*. Ann Vasc Sur. Nov. 1991; 5(6): 491-9.

Marin ML, Veith FJ, Panetta TF, Cynamon J, Barone H, Schonholz C, Parodi JC. *Percutaneous transfemoral insertion of a stented graft to repair a traumatic femoral arteriovenous fistula* J Vasc Surg. Aug. 1993; 18(2): 299-302.

Marin ML, Veith FJ, Panetta TF, Cynamon J, Bakal CW, Suggs WD, Wengerter KR, Barone HD, Schonholz C, Parodi JC. *Transfemoral endoluminal stented graft repair of a popliteal artery aneurysm*. J Vasc Surg. Apr. 1994, 19(4): 754-7.

Chuter TA, Gree RM, Ouriel K, Fiore WM, DeWeese JA. *Transfemoral endovascular aortic graft placement*. J Vasc surg Aug. 1993; 18 (2): 185-95; discussion 195-7.

May J, White G, Waugh R, Yu W, Harris J. *Treetment of Complex abdominal aortic aneurysms by a combination of endoluminal and extraluminal aortofemoral grafts*. J Vasc Surg. May 1994; 19(5): 924-33.

Balko A, Piasecki GJ, Shah DM, Carney WI, Hopkins RW, Jackson BT *Transfemoral placement of intraluminal polyurethane prosthesis for abdominal aortic aneurysm* J Surg Res Apr. 1986; 40(4): 305-9.

Excerpt from Surgical Treatments from Endstage Heart Failure Article. Asian Cardiovascular & Thoracic Annals 2001, vol. 9, No. 3, p. 162.

ABIOMED news release entitled ABIOMED announces FDA Approvals for BVS-5000 Cardiac Support System.

International Search Report of Application No. PCT/US03/15242 dated Sep. 24, 2003.

* cited by examiner

METHOD FOR INSERTING A PROSTHESIS

This application is a divisional application of Ser. No. 10/176,834 filed Jun. 21, 2002 now abandoned.

FIELD OF THE INVENTION

The present invention relates generally to endoluminally implantable luminal prostheses, and more specifically to such prostheses which are implantable into a body lumen, particularly a blood vessel, without using a solid outer sheath during placement.

BACKGROUND OF THE INVENTION

Prostheses which are used to restore dilation or repair otherwise damaged body lumens (such as blood vessels) are known. Typically these prostheses comprise a tubular graft comprised of woven or molded polymeric material, optionally supported in whole or in part by an interiorly or exteriorly disposed mechanical support structure usually referred to as a stent. Prostheses used for this purpose may be introduced percutaneously at an access location remote from a location in a body lumen where the prosthesis is needed but in endoluminal communication therewith. For this purpose, the prosthesis is compressed and held in the compressed state until it has been moved endoluminally to the site in need of repair, where it is expanded and secured. Expansion may be effected, either mechanically by means such as a balloon catheter, or automatically under an elastic or phase change force.

Typically, the prosthesis is retained, in its first configuration, in an outer sleeve or sheath, which may be retained in, or may actually be the forward end of, a delivery catheter. Such a delivery catheter is introduced at the access location and maneuvered through the luminal system to the site where the prosthesis is needed. When the prosthesis reaches that location, it must either be ejected from the delivery catheter, or held in place, while the delivery and/or any surrounding sleeve is retracted.

Another method comprises compressing the prosthesis to a reduced cross-section and then pushing it, in the compressed state, into a catheter which has been previously inserted into the patient. A pusher is used to push the compressed endoprosthesis through the catheter and out the distal end where it expands into place. One drawback of this method is that considerable force must be exerted on the device as it is pushed through the catheter to overcome frictional forces along the lumen. In each of these cases, the cross section of the prosthesis and surrounding catheter, by which it is transported to the deployment location, is a factor which contributes to difficulties in use and deployment of such systems.

In one particular application of such prostheses, an abdominal aortic aneurysm is treated. Such an aneurysm usually occurs in the infrarenal portion of an arteriosclerotically diseased aorta, between the renal arteries and the two iliac arteries, sometimes extending across the aortic bifurcation into one or both iliacs. Typical prostheses for the repair of this region include bifurcated tubular grafts or stent grafts having an aortic section, (typically a section of the prosthesis adapted to be disposed within the aneurysm) and two iliac sections which extend from the aortic section into the iliac arteries. Methods are known which include inserting a bifurcated graft prosthesis endoluminally through one iliac artery and securing it to the aorta by expansion of a stent which is a part of the prosthesis.

It is also known to compress a self-expanding tubular stent-graft and restrain it against a self-expansion force in its reduced cross section configuration, relative to its expanded state, by a knitted strippable sheath. After the sheathed prosthesis is inserted into place within the body, a filament of the sheath is pulled distally to de-knit the sheath and permit its removal as a single filament strand from the prosthesis, allowing the prosthesis to expand to a cross section corresponding to its in-use position. Known sheaths include meshworks of crocheted material extending over the entire length of the prosthesis. One drawback of such an arrangement, however, is that once the drawstring is pulled, expansion of the supporting stent prevents further adjustments of the position of the prosthesis relative to the surrounding lumen.

SUMMARY OF THE INVENTION

The present invention includes a graft system for intraluminal delivery in a body lumen in need of repair. The system comprises a graft, a means for radially expanding the graft and a means for securing at least one end of the graft to the lumen in need of repair (those means optionally comprising a balloon expandable barbed stent disposed in at least part of the graft), and a strippable sheath around at least part of the graft. The strippable sheath, which obviates the need for a hard outer sheath to restrain the prosthesis in its compressed configuration, is removable. Depending upon the type of strippable sheath used, it may be removable by pulling a drawstring to untie or unknit it. In one embodiment, where a scored plastic sheath is used, the scored plastic is unwrapped by initiating the tearing of the scoring of the sheath. A preferred embodiment uses a tied crocheted sheath which is removed by pulling on a drawstring which unties the entire sheath to permit expansion of the graft.

A preferred embodiment of the invention includes a bifurcated graft system for endoluminal delivery in an aortic aneurysm comprising a bifurcated graft having an aortic section and two iliac legs, an expandable stent disposed near the end of the aortic section, and a strippable crocheted sheath around the aortic section and one of the two legs. The strippable crocheted sheath is removable by untying it to permit expansion of the graft after initial placement within the aneurysm.

Also included in the present invention is a method of inserting a graft system to repair a vessel in need of repair comprising the steps of inserting a catheter into an access location of a body lumen to a location in need of repair, the catheter including the graft system of the present invention at the forward end of an axially disposed push rod, with no hard sheath exterior of the graft itself. Once transported to the deployment location, the drawstring (in the preferred embodiment) is retracted to cause untying of a strippable crocheted sheath to allow expansion of the graft. The graft is then positioned, by positioning means such as radiopaque markers and an imaging system, and the graft is then dilated, by, for example, a balloon expandable stent with barbs at the end thereof. In this way, the graft is anchored within the vessel. The catheter is then removed.

BRIEF DESCRIPTION OF THE DRAWINGS

The features of the invention believed to be novel and the elements characteristic of the invention are set forth with particularity in the appended claims. The figures are for illustration purposes only and are not drawn to scale. The invention itself, however, both as to organization and method of operation, may best be understood by reference to the detailed description which follows taken in conjunction with the accompanying drawings in which:

DETAILED DESCRIPTION OF THE INVENTION

Figure 1:
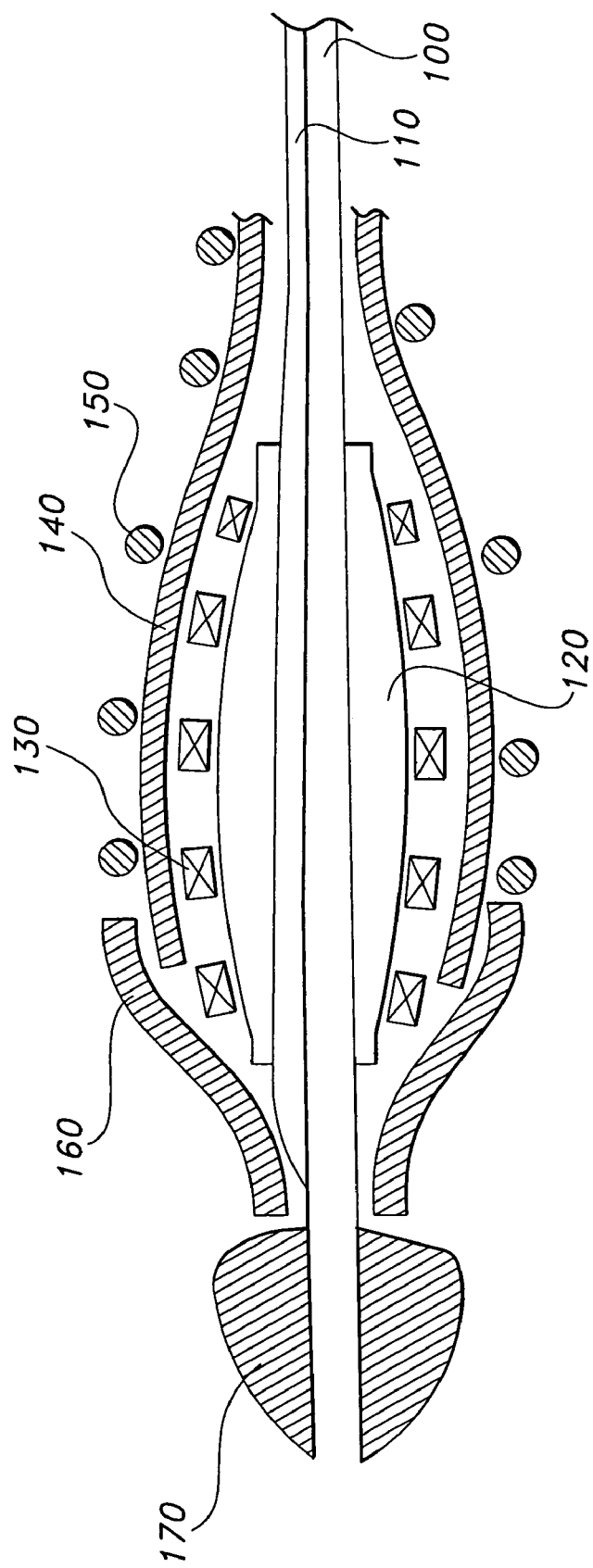
FIG. 1 is a cross section of the proximate end of a device according to the present invention showing, among other things, the compressed graft held in place by a strippable crocheted sheath.

The present invention includes a graft system and method for its use to repair a diseased or otherwise defective body lumen. A preferred embodiment of the present invention includes a graft system for intraluminal delivery in a vessel in need of repair comprising a graft, a radial expansion means to expand the graft to its fully dilated configuration (preferably a balloon expandable stent disposed within at least part of the graft), and a strippable crocheted sheath around at least part of the graft. The strippable crocheted sheath is removable to permit expansion of the graft and stent. Included as a part of the invention is a bifurcated graft system for intraluminal delivery in an aortic aneurysm in need of repair comprising a bifurcated graft having a distal region and two legs, a balloon expandable stent disposed in part of the distal region, and a strippable crocheted sheath around the distal region and one of the two legs. The strippable crocheted sheath is removable (by unraveling or untying) to permit expansion of the graft and stent after initial placement within the aneurysm.

Different embodiments include different means for securing the first end of the graft to the aorta. Generally, the securing means has a first diameter which permits intraluminal delivery of the securing means into the aorta and a second, expanded diameter, to secure the first end of the graft to the aorta. A preferred securing means is a balloon-expandable stent. The stent used in the device of the present invention is not completely self-expandable, but may be either completely balloon-expandable or partially self-expandable and partially manually expandable (such as with a balloon). The stent is fully deployed using a radial expansion means for expanding the stent and graft to a radially expanded configuration.

A radial expansion means is necessary because the present invention does not fully expand automatically upon removal of the sheath. This allows the position of the device to be adjusted prior to fully dilating the stent, but after removal of the delivery sheath. Other options for the expansion means include using a stent made from a material which is self-expandable at temperatures higher than body temperature. Such materials can be used where heat is added at the site of deployment when dilation is desired to warm the device to a temperature in excess of body temperature such that self-expansion will occur after the sheath has been removed. Such a heat-activated expansion contemplates the application of heat after the sheath is removed for a controlled expansion after placement. In such a case, the material would be used with the present invention without a balloon expansion device, or in combination with a balloon (e.g. where the initial expansion, prior to heat application, is through the use of a balloon). An important part of the present invention is that the stent and related parts of the device not automatically expand completely after the strippable sheath is removed.

In a preferred embodiment, the delivery sheath is a strippable sheath that covers at least part of the graft, the strippable sheath maintaining the graft in the reduced profile prior to, and during, insertion into the passageway in need of repair. A preferred strippable sheath is a crocheted strippable sheath with a drawstring extending from the strippable sheath. Upon pulling the drawstring at the lumen access location, the crocheted sheath is untied, or removed, permitting expansion of the graft and related device component(s), first by relaxation and then by a radial expansion means such as a balloon expander acting directly on the graft or balloon expandable stent. In another embodiment, the strippable sheath is a scored plastic sheath which is removed by tearing of the scoring of the sheath and pulling the torn plastic sheath out of the body lumen from the point of insertion. Other embodiments would include a quickly biodegradable sheath, such as a polyvinylalcohol (PVA) sheath, although this embodiment must be carefully used as precise control over the timing of sheath removal can introduce a variable into the system deployment procedure.

It is noted that in this specification, "proximal" shall mean closest to point of insertion, and "distal" shall mean furthest from the point of insertion.

FIG. 1 shows the distal end of a device in accordance with the present invention. Guidewire lumen 100 (for a guidewire which is not shown) is accompanied by balloon dilation lumen 110 for inflating balloon 120. Disposed around balloon 120 is stent 130, which is shown in its compressed state. Graft 140 is disposed atop stent 130 and is shown as held in its compressed state by strippable crocheted sheath 150. Materials which are suitable for the graft are well known to those skilled in the art and include for example woven polyester and molded expanded polytetrafluoroethylene.

Soft elastic tube 160 is also shown disposed between catheter tip 170 and graft 140. Soft elastic tube 160 combines with rounded catheter tip 170 to provide a relatively smooth, easily insertable end to the overall device. Soft elastic tube 160 is typically made of silicone. Thus, as the catheter and its components are threaded through the body lumen along a guidewire, damage to the lumen is minimized.

Figure 2:
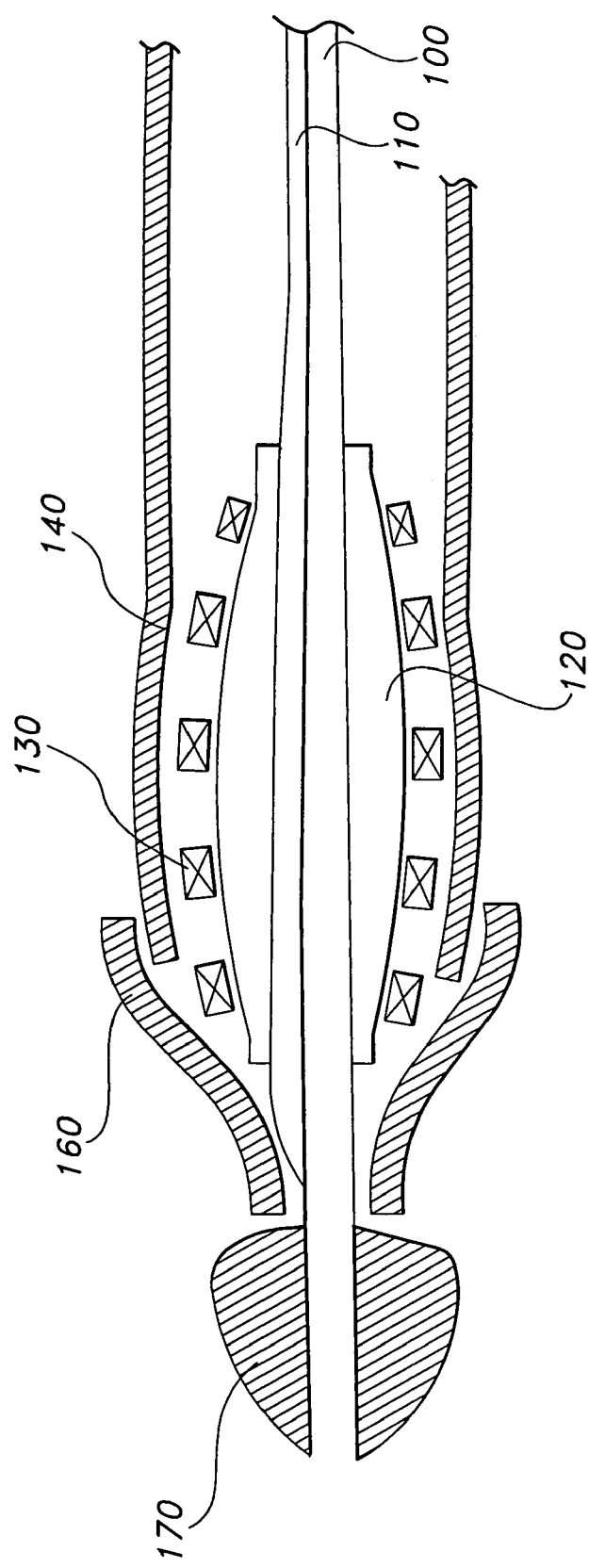
FIG. 2 is the same as the device of FIG. 1 except without the strippable crocheted sheath.

FIG. 2 shows the same view as FIG. 1 but with strippable crocheted sheath 150 removed. In this figure, it can be seen that graft 140 has been allowed to expand to a relaxed configuration. This relaxed configuration is one which graft 140 would have had but for the restraint applied to it by strippable crocheted sheath 150. Had the device been inserted into the body lumen without strippable crocheted sheath 150 in place over graft 140, insertion would have been much more traumatic for the patient. Without strippable crocheted sheath 150, graft 140 would be allowed to expand and would create a looser, larger, and more cumbersome profile, reducing the ease with which the overall device can be inserted. Included among the problems that would result without use of strippable crocheted sheath 150 would be kinking and twisting of graft 140 as the catheter is advanced through the relatively tortuous passageway leading to the desired site of implantation. This is especially true when the diseased lumen to be treated is an aortic aneurysm.

Figure 3:
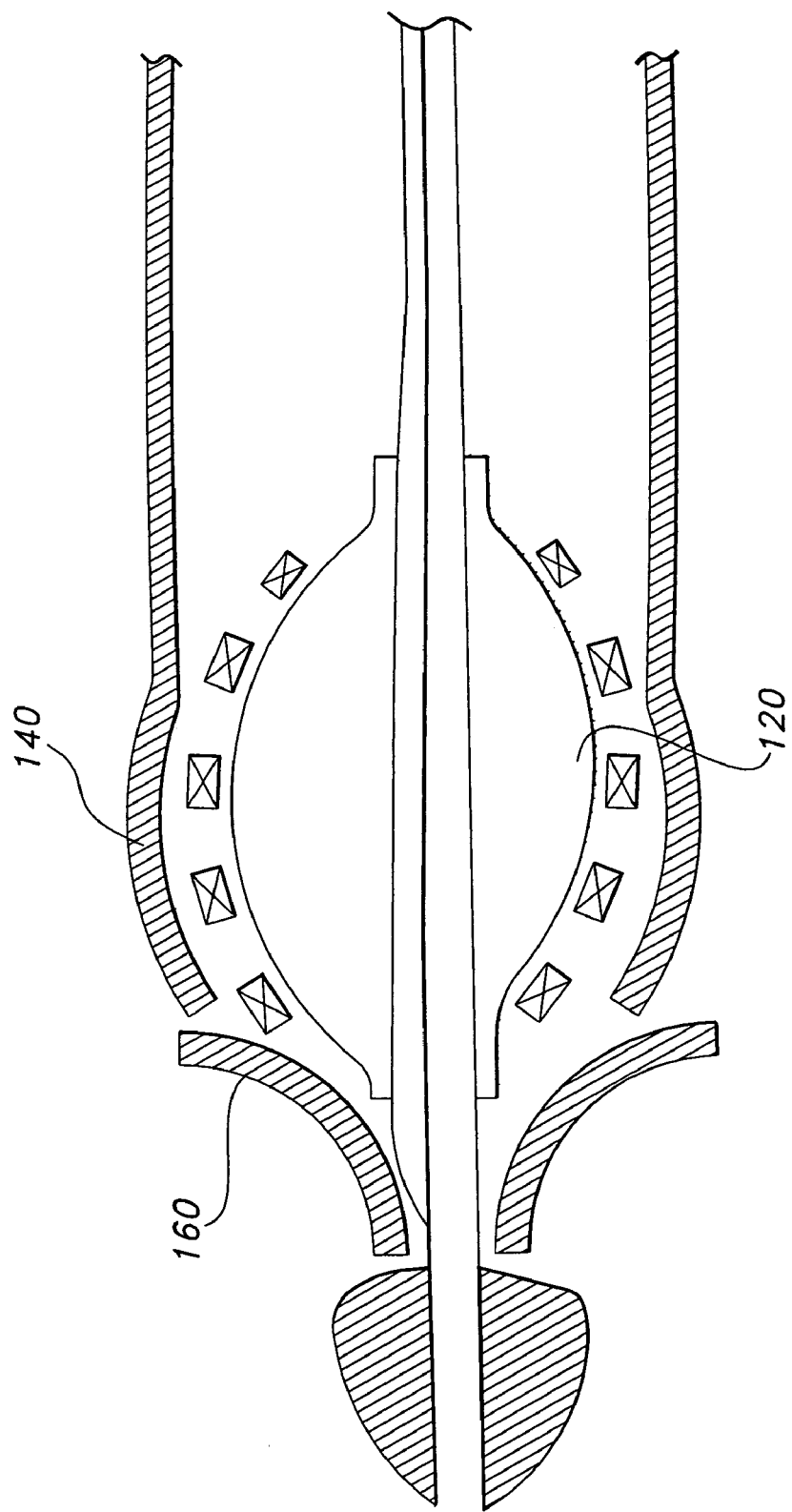
FIG. 3 is shows the device of claim 2 during the initial stage of stent dilation through balloon inflation.
Figure 4:
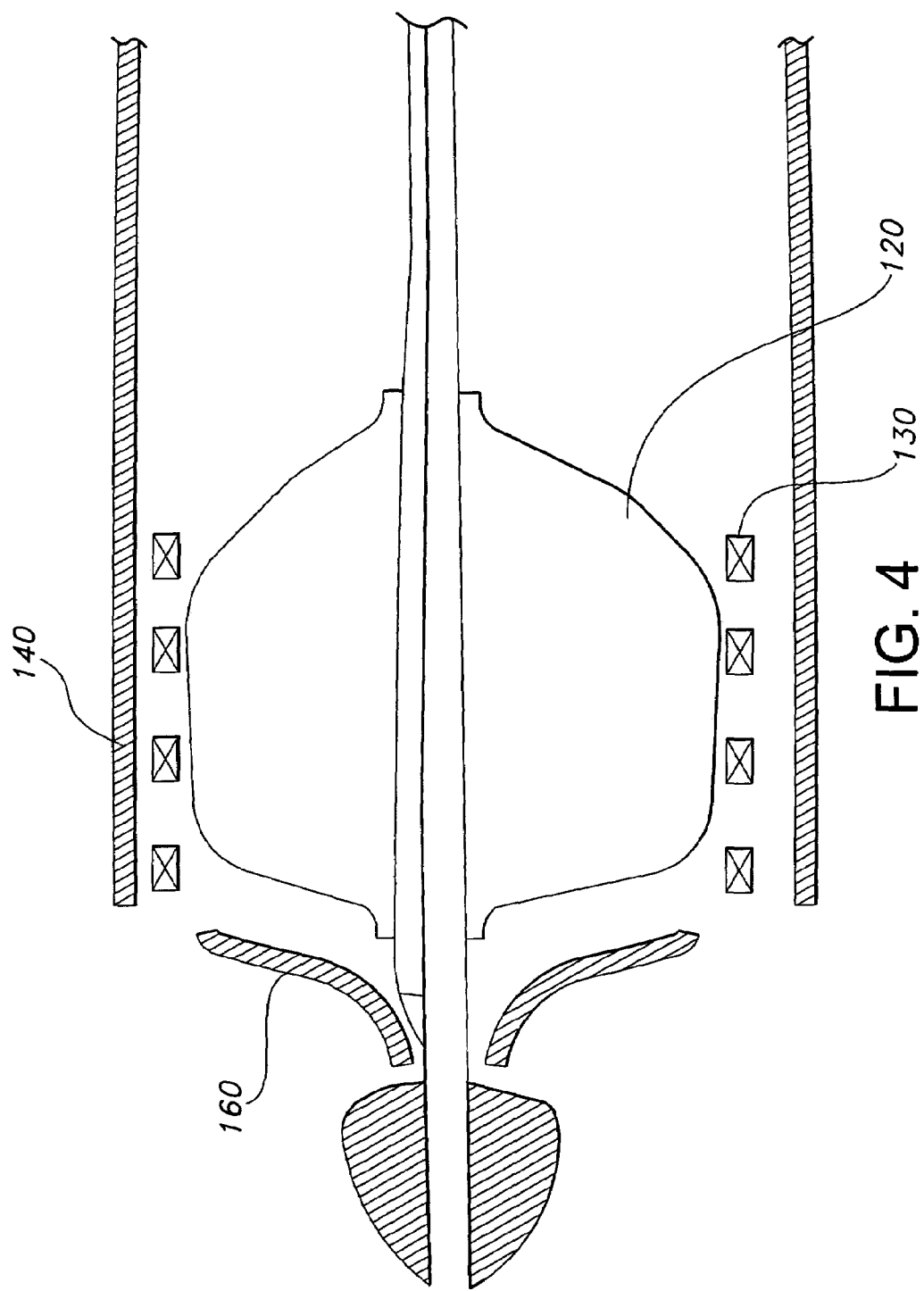
FIG. 4 shows the balloon fully inflated and the stent fully dilated.
Figure 5:
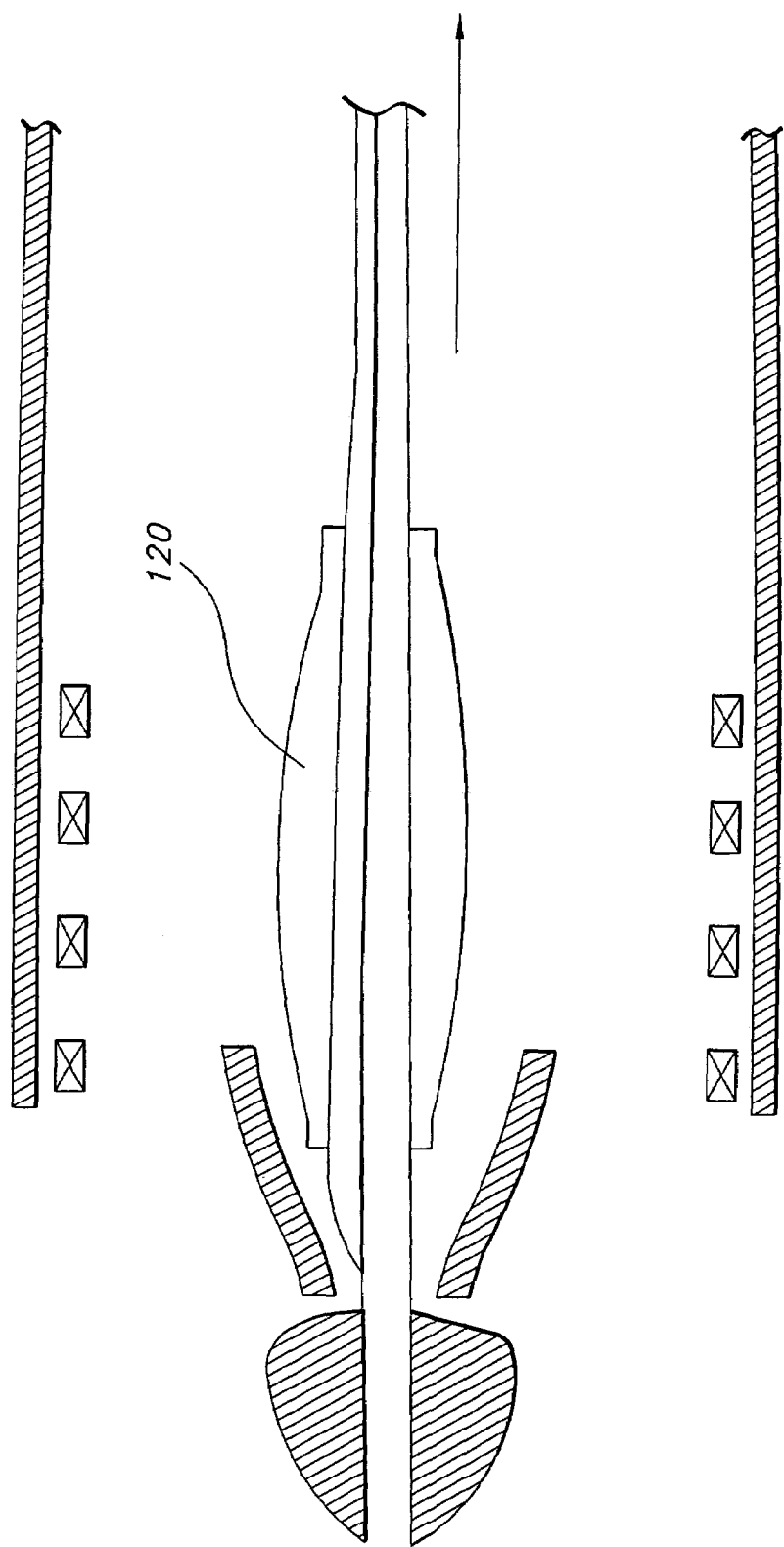
FIG. 5 shows the balloon deflated and the deployment device about to be removed.

FIG. 3 shows the same view as FIG. 2 but with balloon 120 partially expanded. This view shows, among other things, the distal end of graft 140 pulling out from under soft elastic tube 160 as balloon 120 expands outwardly. FIG. 4 shows balloon 120 fully expanded with stent 130 and graft 140 in place within a lumen (not shown). Soft elastic tube 160 is now inside the diameter of graft 140 (although it would not have to be inside the diameter at this point, so long as it is able to be removed from the inside of graft 140 when the catheter/delivery device is removed from the site of deployment). FIG. 5 shows balloon 120 deflated and the device ready for removal in the direction of the arrow shown.

Also included in the present invention is a method of inserting a graft system to repair a vessel in need of repair comprising the steps of inserting a catheter into a vessel to a location in need of repair, the catheter including the graft system of the present invention, retracting the drawstring to cause untying of the strippable crocheted sheath to allow expansion of the graft, expanding the stent to anchor the stent and the graft within the vessel, and then removing the catheter.

Figure 6:
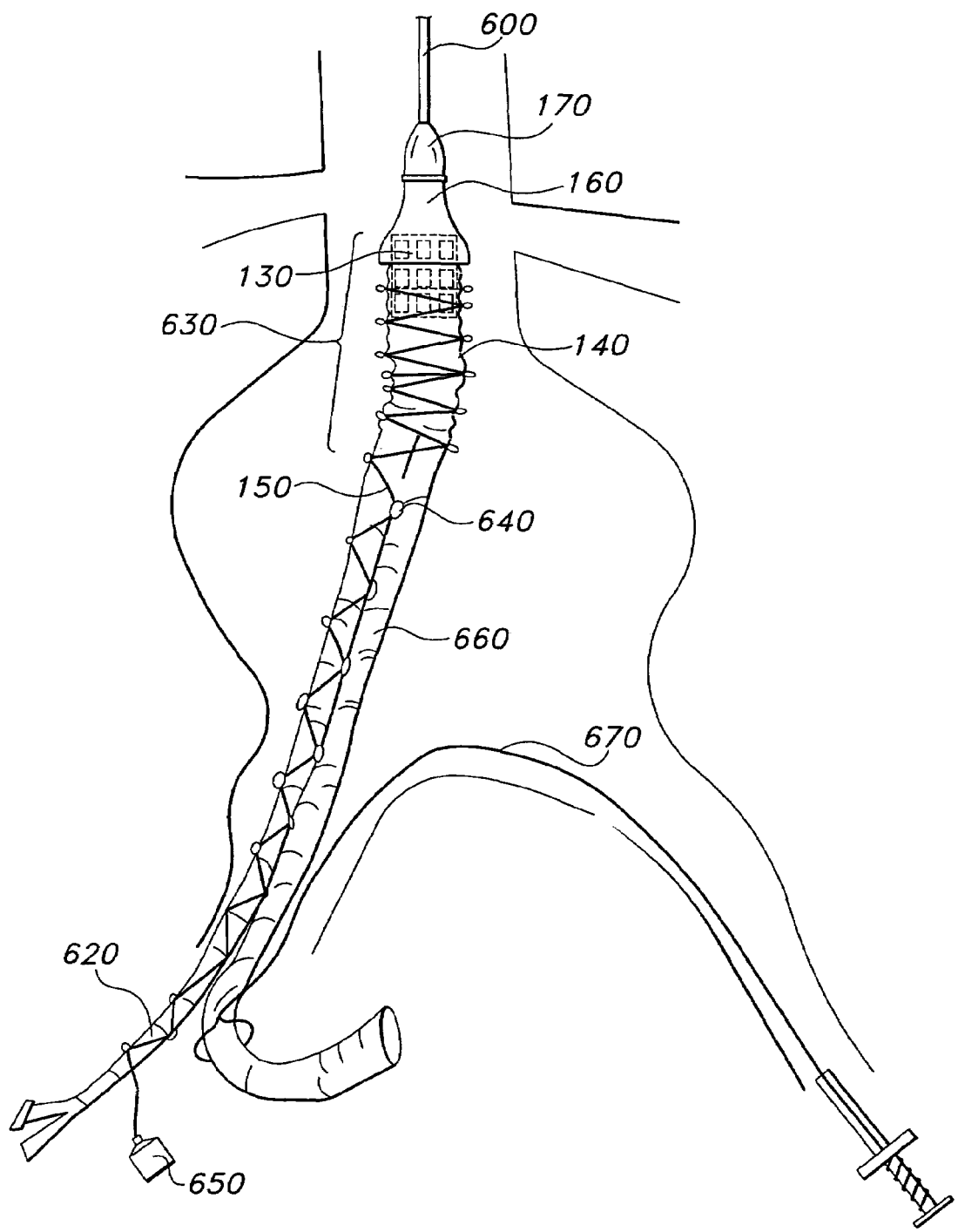
FIG. 6 shows an early step in device placement where the strippable crocheted sheath is disposed around part of the graft, holding it against its relaxed state.

FIG. 6 shows the initial placement of the device within an aortic aneurysm. Guidewire 600 is inserted first according to methods known in the prior art, and then the catheter holding the device is advanced along guidewire 600 into position as shown in FIG. 6. Catheter tip 170 is shown distal to soft tube 160, with stent 130 disposed within the distal end of graft 140. Strippable crocheted sheath 150 runs along first iliac leg 620 and over graft distal region 630 (which is the non-bifurcated region of graft 140). Knots 640 are disposed along strippable crocheted sheath 150 which hold strippable crocheted sheath 150 in place until drawstring 650 is pulled. The presence of strippable crocheted sheath 150 maintains graft 140 in its reduced diameter, allowing easier advancement of the device over guidewire 600, as discussed above.

Methods and products are known for tying strippable crocheted sheath into place over graft 140. Among such methods and products is that disclosed in detail in U.S. Pat. No. 6,019,785 to Strecker, which is hereby incorporated herein by reference. In these methods and products, when a single drawstring is pulled by the surgeon, the sheath unravels, or otherwise unties, allowing the graft material to assume a relaxed and expandable configuration.

Figure 7:
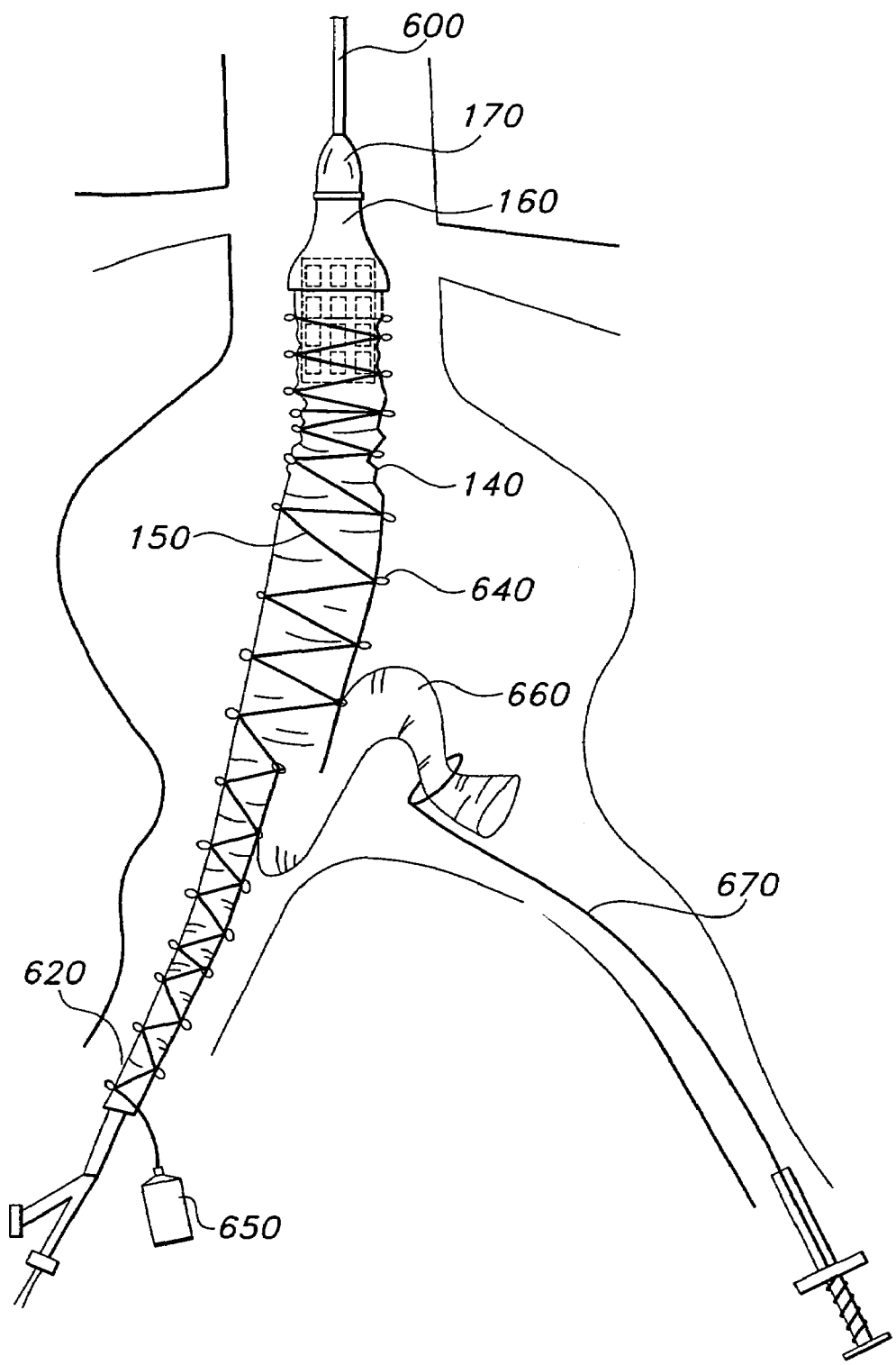
FIG. 7 shows a subsequent step where a contralateral limb is pulled into an adjacent iliac artery.
Figure 8A:
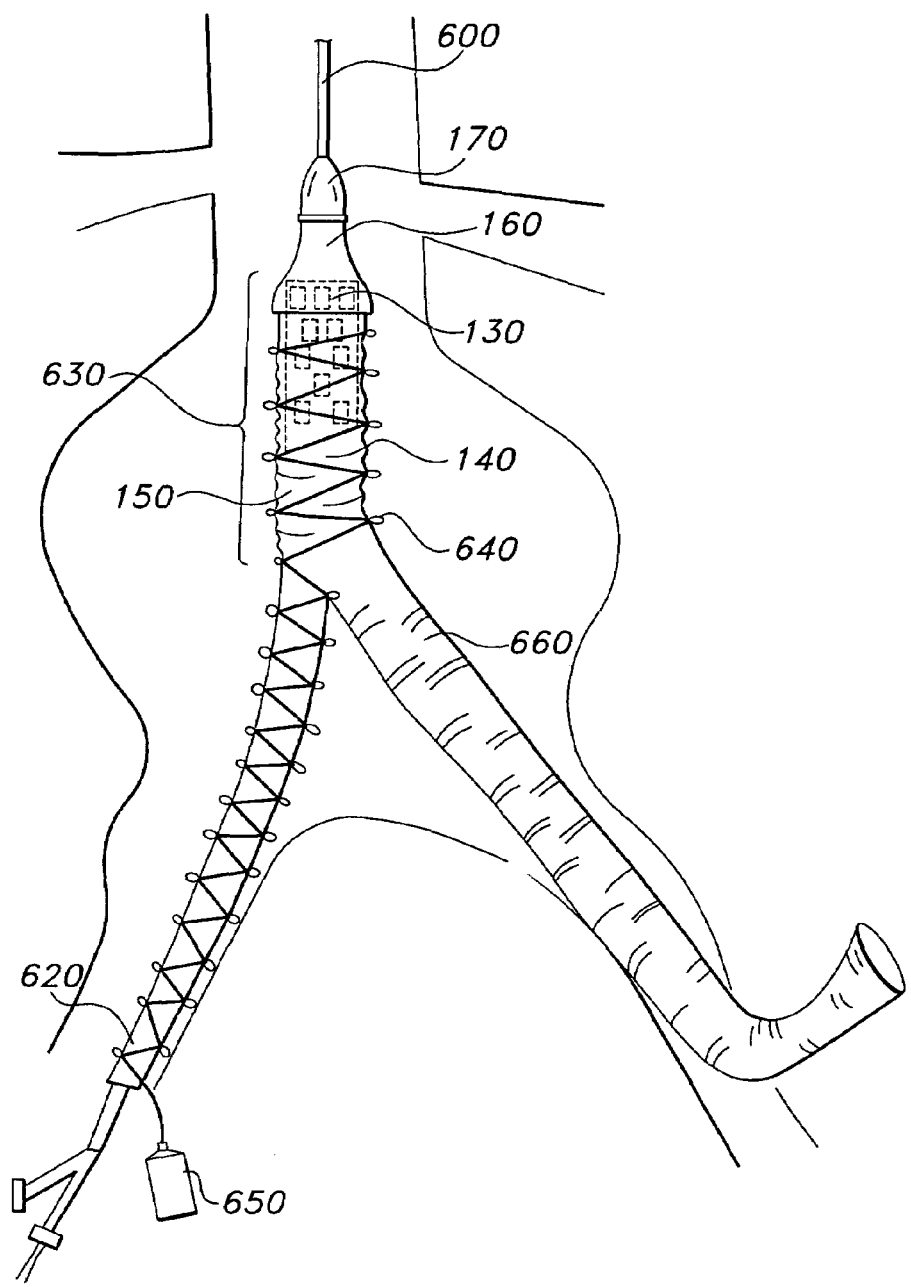
FIG. 8A shows the device in place just prior to removal of a strippable crocheted sheath which covers the distal trunk portion and one iliac leg.

As shown in FIGS. 6 and 7, for example, contralateral limb 660 is not covered by strippable crocheted sheath in this embodiment. FIG. 7 shows grasping snare 670 pulling contralateral limb 660 into its iliac artery to achieve the desired placement of the bifurcated device. Once contralateral limb 660 is in place, the configuration as shown in FIG. 8A is achieved. In an alternative embodiment, grasping snare 670 may be unnecessary. In such an alternative, the device could be advanced distally to a point beyond its final placement such that the distal end of contralateral limb 660 passes the aortic bifurcation. Then, prior to full expansion of the prosthesis, the entire device could be moved distally while guiding the contralateral limb 660 down into its respective iliac artery.

Figure 8B:
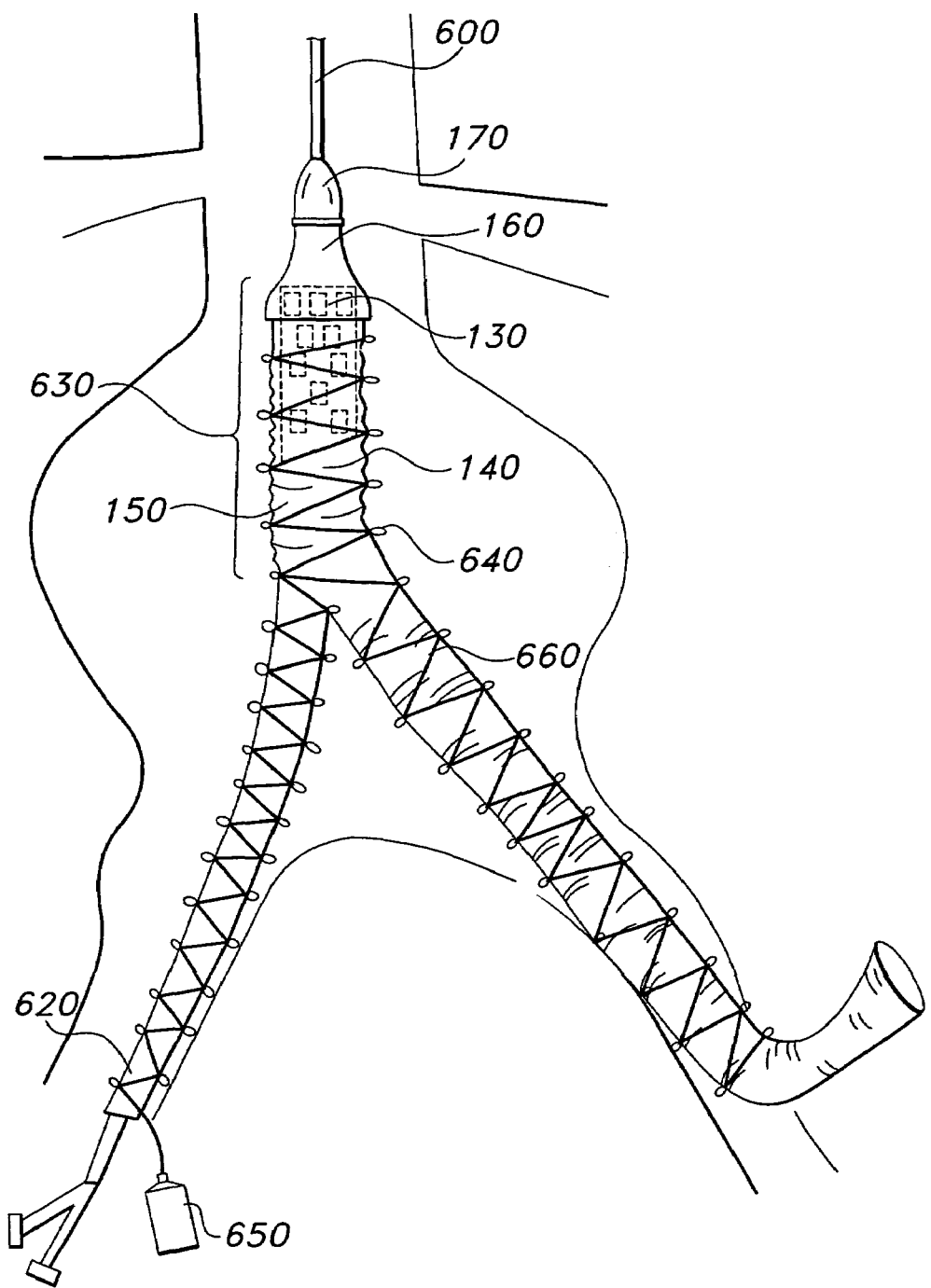
FIG. 8B shows the device in place just prior to removal of a strippable crocheted sheath which covers the distal trunk portion and both iliac legs.
Figure 8C:
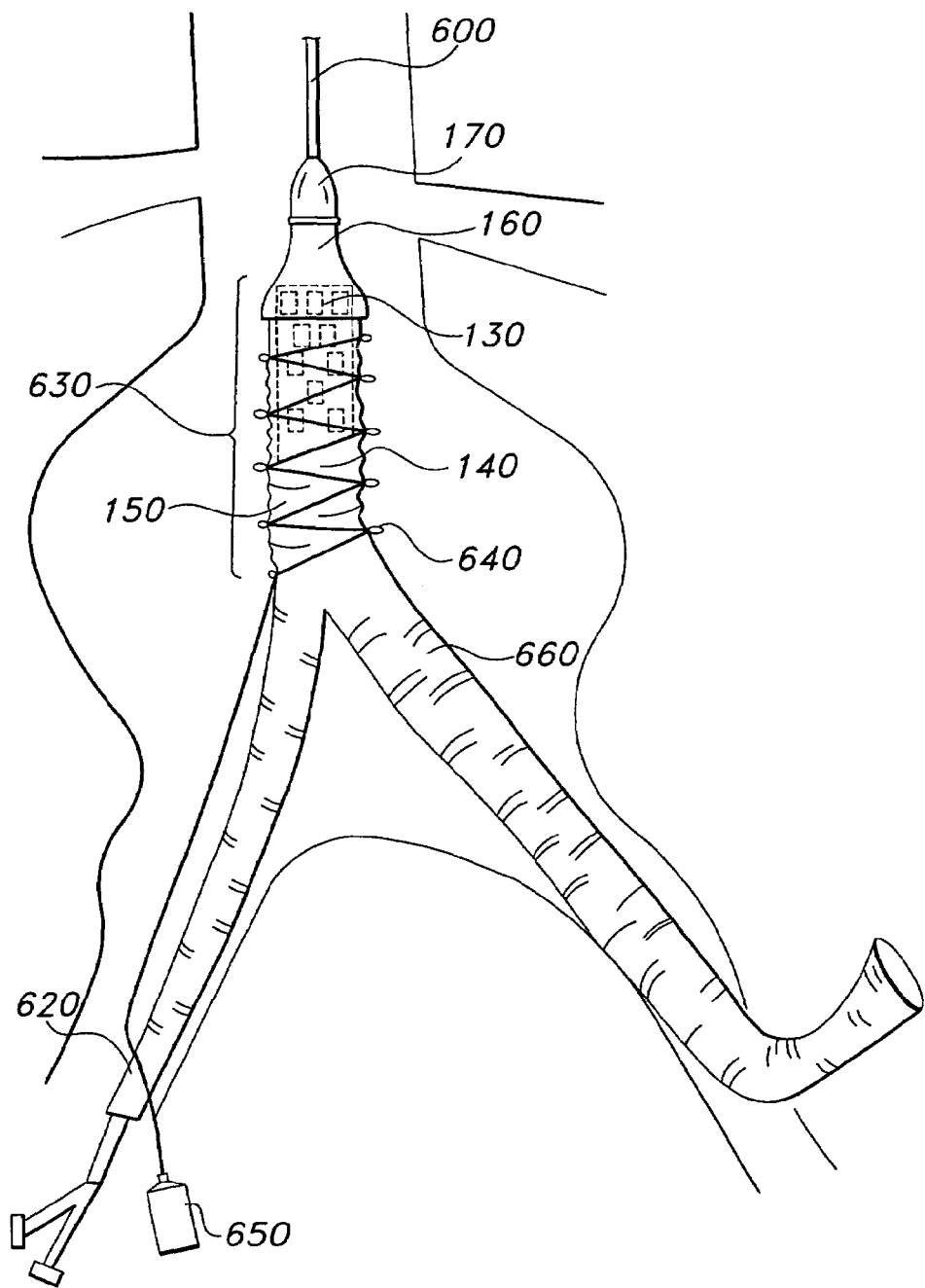
FIG. 8C shows the device in place just prior to removal of a strippable crocheted sheath which covers only the distal trunk portion.

In alternative embodiments, different parts of the graft may be covered by the removable sheath. For example, FIG. 8B shows an embodiment where all of the graft is covered by strippable crocheted sheath 150, and FIG. 8C shows an embodiment where only graft distal region 630 is covered by strippable crocheted sheath 150.

Figure 9:
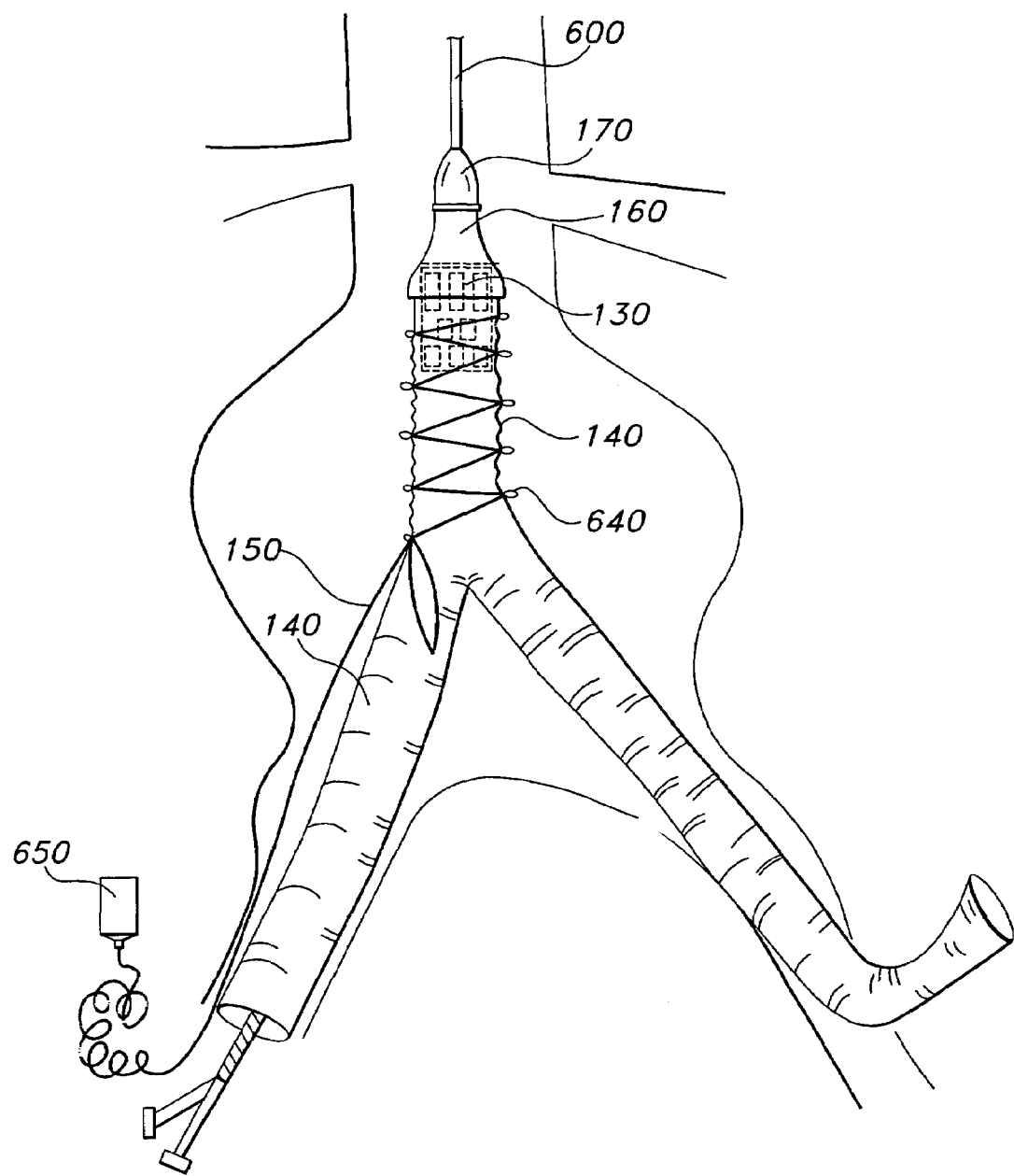
FIG. 9 shows the removal of the strippable crocheted sheath where the drawstring was pulled to untie the sheath.
Figure 10:
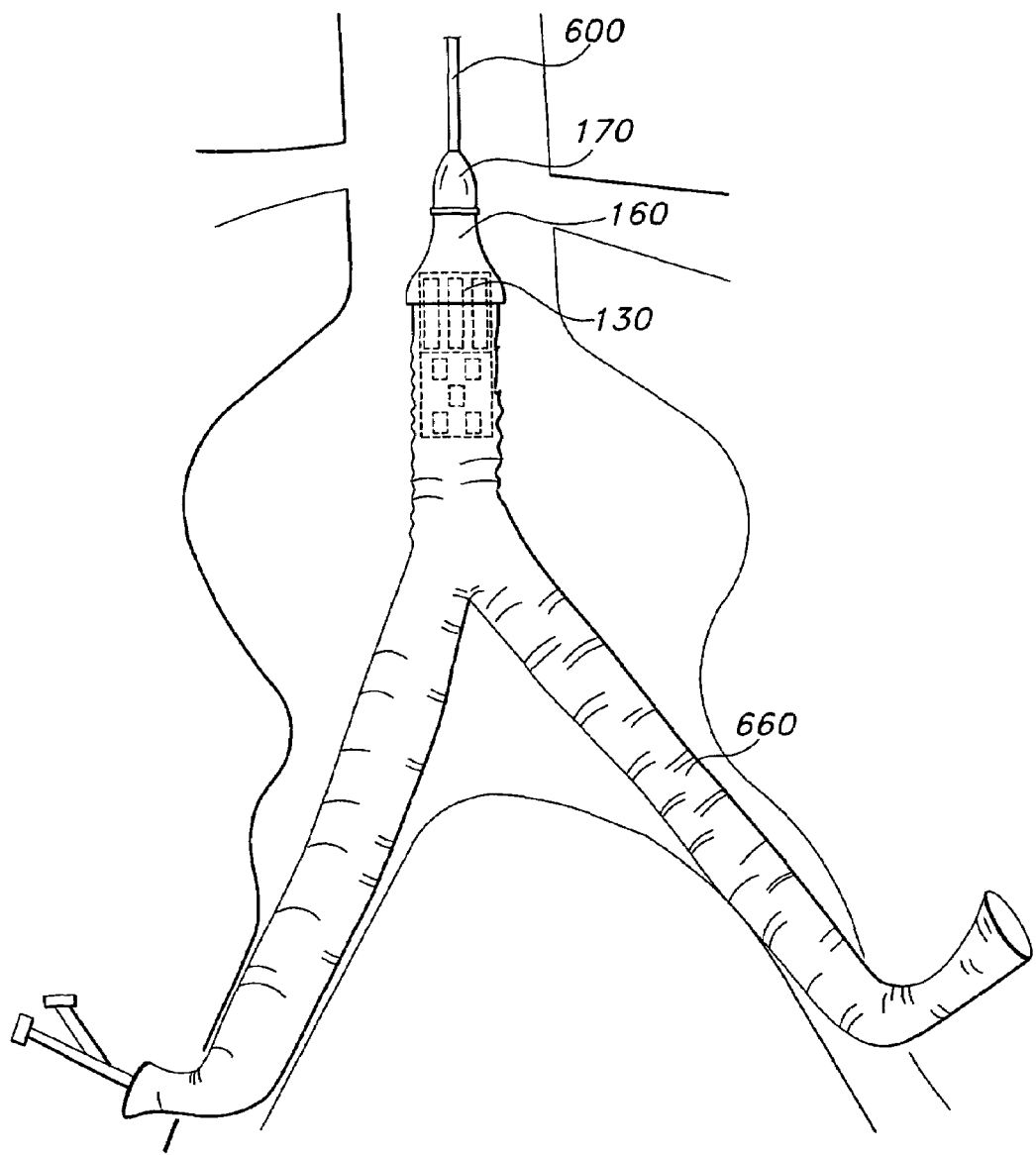
FIG. 10 shows the device with the strippable crocheted sheath removed just prior to dilation of the stent.

FIG. 9 shows the step where drawstring 650 is retracted which results in the untying of strippable crocheted sheath 150. In the present invention, strippable crocheted sheath is untied, graft 140 is no longer constrained and may expand to an intermediate uncompressed state. During expansion, graft 140 shortens somewhat in length. FIG. 10 shows strippable crocheted sheath completely removed, with graft 140 fully relaxed in place within the aneurysm. Stent 130, in this particular embodiment and figure, is now partly exposed at its distal end due to the relative shortening of graft 140 during expansion upon removal of strippable crocheted sheath 150. Other embodiments, however, are contemplated, and include situations where the design and graft material are chosen so that complete coverage of the stent is maintained even after deployment and expansion.

Now that strippable sheath 150 has been removed and the graft has obtained its relaxed dimensions, final adjustments can be made to the exact placement of the device within the aneurysm. This can be done through known visualization techniques, including the use of radiopaque markers disposed on or along the graft or stent for fluoroscopic positioning. Once final placement is achieved, the stent can be expanded to secure the device.

Figure 11:
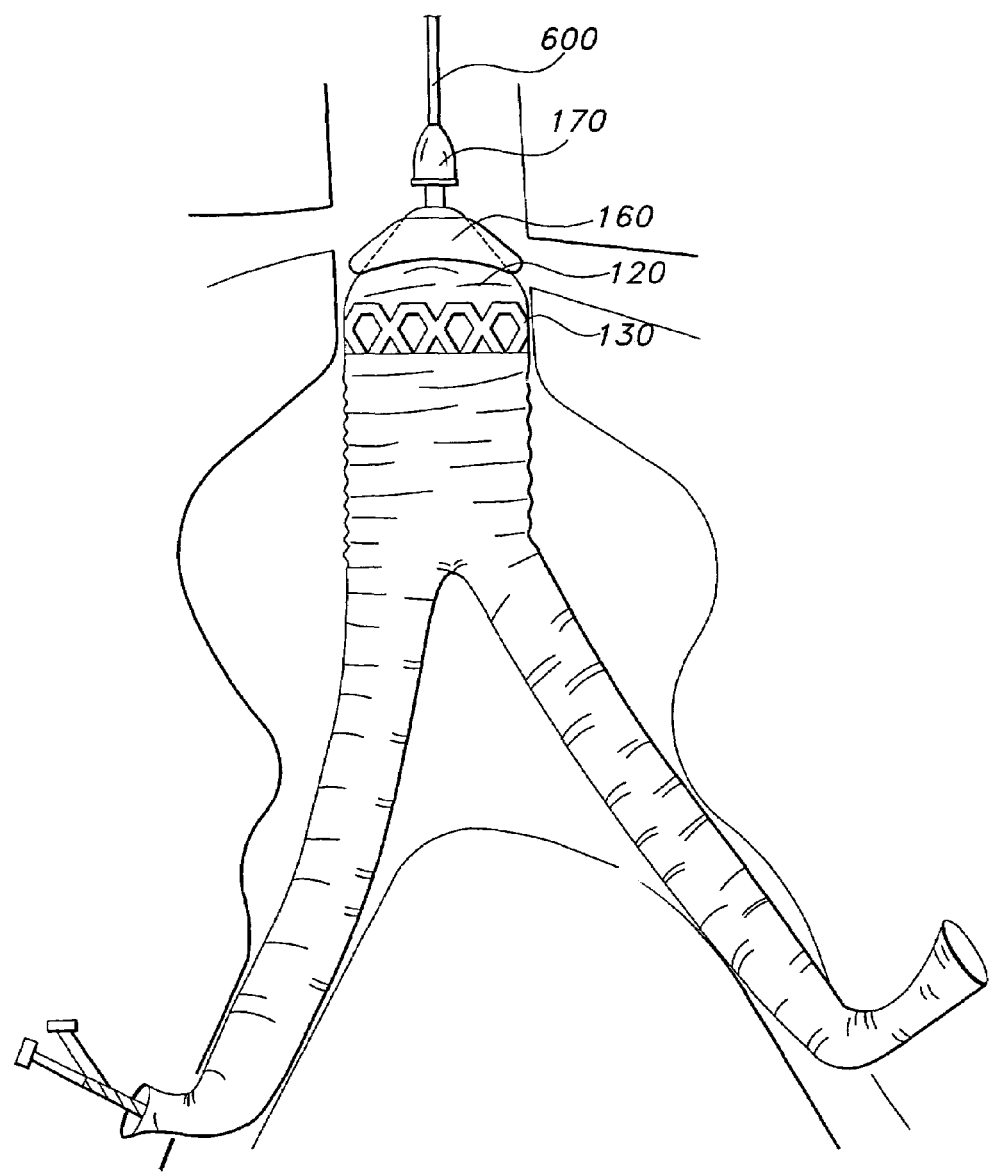
FIG. 11 shows the stent dilation under force of a balloon.
Figure 12:
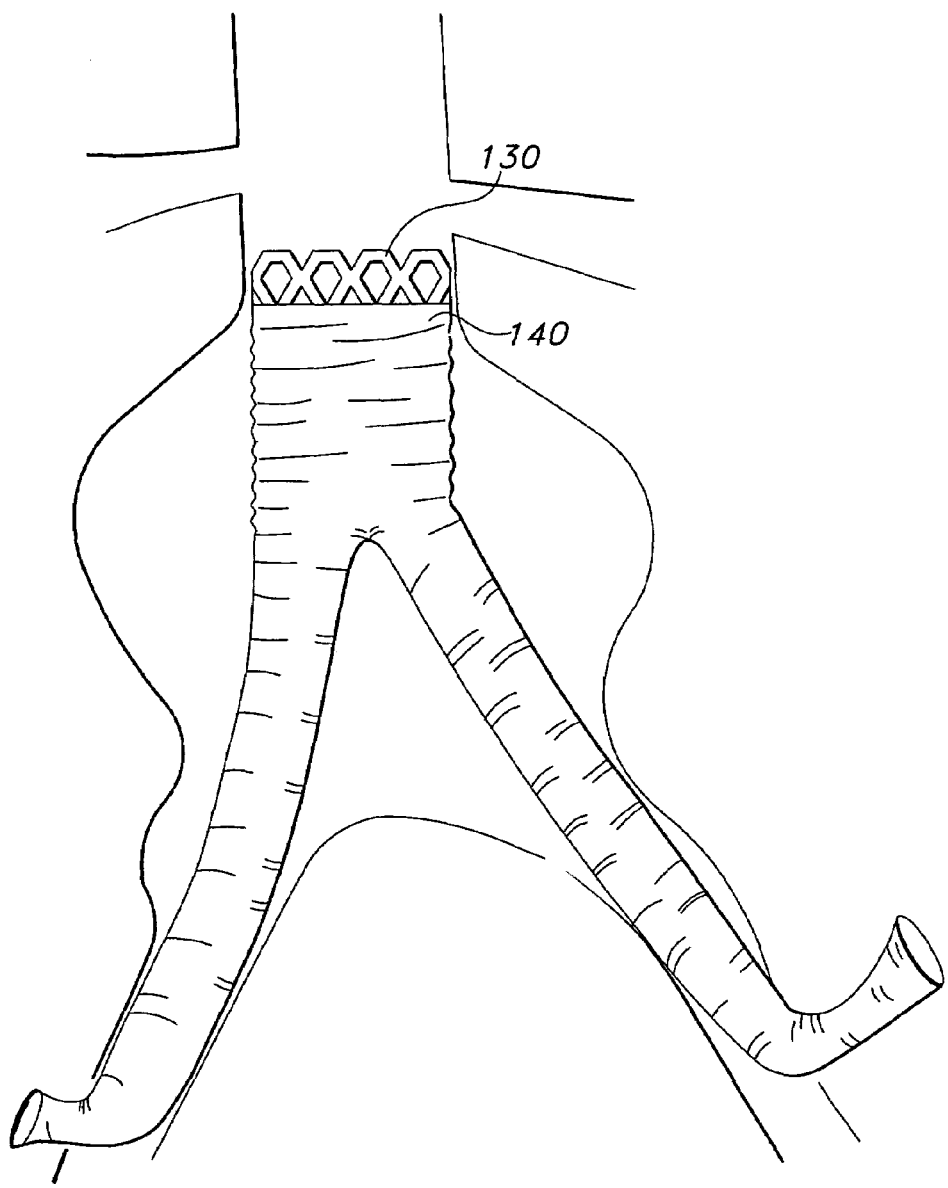
FIG. 12 shows the device in place after stent dilation and catheter removal.

FIG. 11 shows the next step in the deployment process where balloon 120 is expanded to dilate stent 130, expanding the prosthesis to its fully expanded state so that the aneurysm neck portion is occluded by the device. In this embodiment, soft nose 160 expands as stent 130 dilates out of the confines of soft nose 160. Once stent 130 is fully dilated, balloon 120 is deflated and the catheter is removed, leaving stent 130 lodged in the aneurysm neck, with graft 140 ready to receive blood flow, all as shown in FIG. 12.

Figure 13:
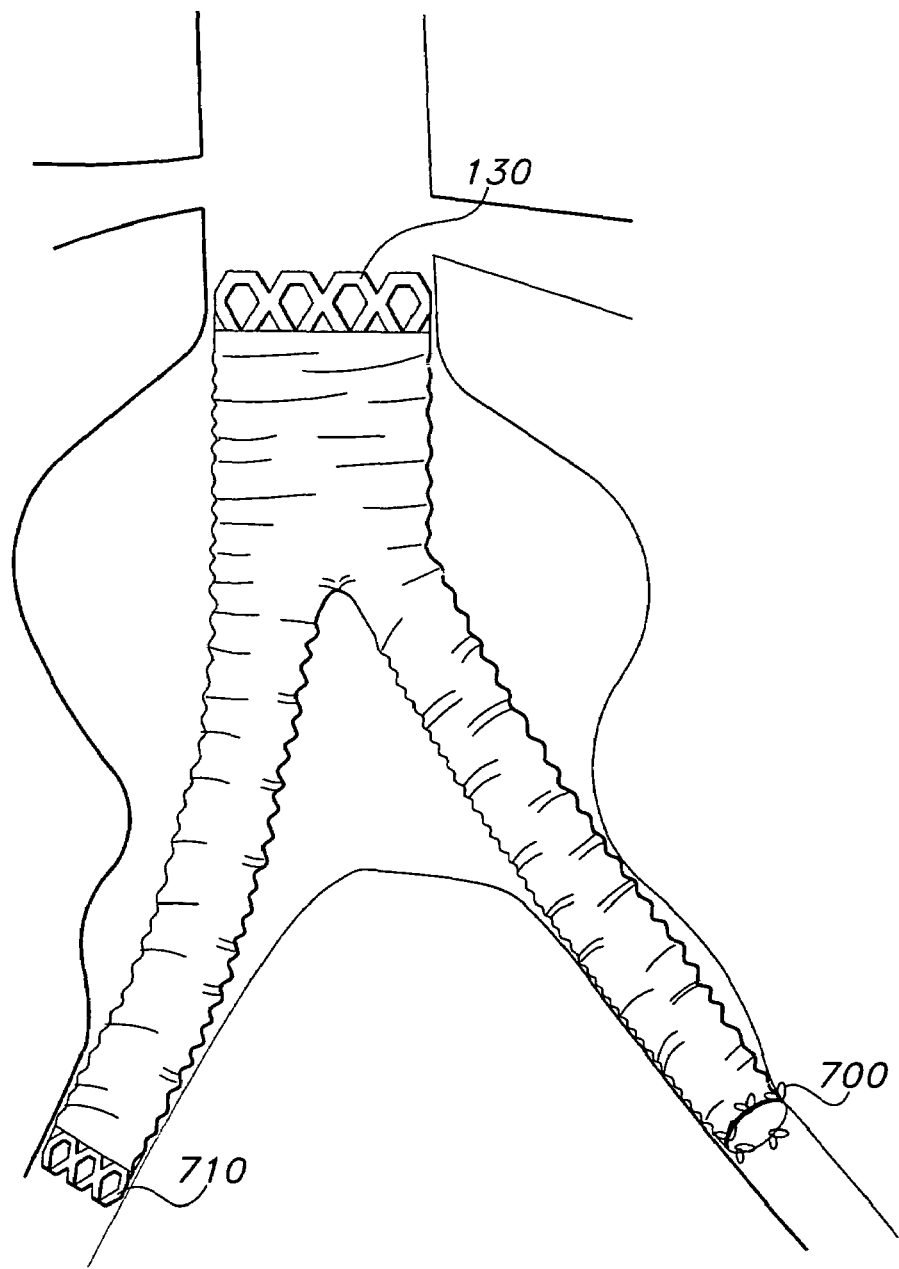
FIG. 13 shows the iliac distal ends secured within the iliac arteries.

FIG. 13 shows a final step whereby the distal ends of graft 140 are attached to their respective iliac artery walls, after some compression of graft 140 to allow for movement caused, for example, by pulsetile blood flow and temporal migration. In this embodiment, simply for purposes of illustration, first iliac leg 620 is stented into place with stent 710, while contralateral limb 660 is sewn into place with sutures 700.

In the embodiment shown in FIG. 13, stent 130 and graft 140 are simply frictionally connected, with graft 140 effectively pinched between stent 130 and the aortic wall. Optionally and preferably, graft 140 may be attached to stent 130. Several methods are known to accomplish this attachment, included sewing, gluing, or otherwise fastening the two together. This is true also for any stents which may be used at the distal ends of one or both of the iliac legs.

In still other alternatives, a mechanical dilation means, such as a push rod actuated cam or umbrella spoke network to forcibly expand the graft, with or without a supporting stent, may be used to expand to graft to its fully dilated configuration. Similarly, the prosthesis may be secured at any end thereof, to the surrounding lumen, by any of a wide variety of attachment means including but not limited to staples, sutures, stents, stents with barbs, deformable T-head plastic fasteners, etc.

Accordingly, while illustrated and described herein with reference to certain specific embodiments, the present invention is not intended to be limited to the embodiments and details shown. Rather, the appended claims are intended to include all embodiments and modifications which may be made in these embodiments and details, which are nevertheless within the true spirit and scope of the present invention.

What is claimed:

1. A method of inserting a graft system to repair a vessel in need of repair comprising the steps of:
    inserting a catheter from a vessel access location into a vessel to a deployment location in need of repair, the catheter having a graft system disposed thereon and not covered by a solid outer sheath, the graft system comprising:
        a centrally disposed push wire surrounded by a graft;
        a non-self-expandable stent disposed in at least part of the graft;
        a strippable string extending circumferentially around at least part of the graft, the strippable string being removable to permit expansion of the graft and stent; and
        a drawstring extending from the strippable string to the access location, wherein retraction of the drawstring results in the untying and removal of the string;
    retracting the drawstring to cause untying and removal of the strippable string;
    expanding the stent to anchor the stent and the graft within the vessel; and
    removing the catheter.

2. The method of claim 1 wherein the stent is a balloon expandable stent and said expanding step comprises inflating a balloon disposed on said catheter.

3. The method of claim 1 wherein the vessel in need of repair is an aortic aneurysm, the graft is bifurcated having a distal region and two distal legs, and the strippable crocheted sheath extends around the distal region and only one of the two distal legs.

4. The method of claim 3 wherein said inserting step is through one iliac artery, and one leg of the graft is not covered by the string, further comprising the step of:
    before said retracting step, pulling the leg not covered by the string into the iliac artery not used to insert the catheter.

* * * * *